United States Patent
Das et al.

(10) Patent No.: US 9,718,746 B2
(45) Date of Patent: Aug. 1, 2017

(54) PROCESS FOR REMOVING OXYGENATED CONTAMINATES FROM AN ETHYLENE STREAM

(75) Inventors: Babua Das, Kolkata (IN); Manuela Arratia, Paris (FR); Catherine Boutrot, Chatou (FR)

(73) Assignees: Total Research & Technology Feluy, Seneffe (BE); IFP Energies Nouvelles, Rueil Malmaison (FR)

( * ) Notice: Subject to any disclaimer, the term of this patent is extended or adjusted under 35 U.S.C. 154(b) by 544 days.

(21) Appl. No.: 14/235,291

(22) PCT Filed: Jul. 13, 2012
(Under 37 CFR 1.47)

(86) PCT No.: PCT/EP2012/063755
§ 371 (c)(1),
(2), (4) Date: Apr. 10, 2014

(87) PCT Pub. No.: WO2013/014003
PCT Pub. Date: Jan. 31, 2013

(65) Prior Publication Data
US 2014/0323791 A1    Oct. 30, 2014

(30) Foreign Application Priority Data
Jul. 28, 2011  (EP) .................................. 11290349

(51) Int. Cl.
C07C 7/04 (2006.01)
C07C 7/12 (2006.01)
C07C 7/00 (2006.01)

(52) U.S. Cl.
CPC ............... C07C 7/005 (2013.01); C07C 7/04 (2013.01); C07C 7/12 (2013.01); Y02P 30/464 (2015.11)

(58) Field of Classification Search
None
See application file for complete search history.

(56) References Cited

U.S. PATENT DOCUMENTS 6,444,869 B2    9/2002   Senetar et al.
9,328,297 B1 *  5/2016   Nyce ...................... C10G 50/00
(Continued)

FOREIGN PATENT DOCUMENTS

WO    01/25174 A1    4/2001
WO    03/020670 A1    3/2003
(Continued)

OTHER PUBLICATIONS

Office Action issued in Ukrainian Patent Application No. a 201401713, dated Dec. 29, 2015, 7 pages.
(Continued)

Primary Examiner — Tam M Nguyen
(74) Attorney, Agent, or Firm — Albert Shung

(57) ABSTRACT

The present invention is a process for removing oxygenated contaminants from an ethylene stream comprising:
a) providing a dried ethylene stream (A) comprising essentially ethylene, up to 1 w % oxygenates, ethane, CO, $CO_2$, $H_2$, $CH_4$ and C3+ hydrocarbons,
b) sending said stream (A) to a C2 splitter/deethanizer to produce
a bottom stream comprising essentially ethane, oxygenates and C3+ hydrocarbons,
an overhead comprising the remaining components,
c) sending said overhead to a fixed bed $CO_2$ adsorption zone to recover a stream essentially free of $CO_2$,
d) sending said stream essentially free of $CO_2$ to a demethanizer/CO stripper to recover an overhead comprising $H_2$, $CH_4$ and CO, liquid ethylene at the bottoms.
In another embodiment the $CO_2$ removal step can be made on the recovered ethylene.

29 Claims, 5 Drawing Sheets

(56) References Cited

U.S. PATENT DOCUMENTS

2003/0098281 A1   5/2003  Shutt et al.
2005/0283038 A1  12/2005  Kuechler et al.
2014/0303422 A1* 10/2014  Das .................. C07C 7/005
                                             585/809
2015/0330706 A1* 11/2015  Vermeiren ............ C07C 1/24
                                             62/620

FOREIGN PATENT DOCUMENTS

| WO | 03/020672   A1 | 3/2003 |
| WO | 03/033438   A1 | 4/2003 |
| WO | 2004011404  A1 | 2/2004 |
| WO | 2008042613  A2 | 4/2008 |
| WO | 2009/098262 A1 | 8/2009 |
| WO | 2009/098267 A1 | 8/2009 |
| WO | 2009/098268 A1 | 8/2009 |
| WO | 2009/098269 A1 | 8/2009 |

OTHER PUBLICATIONS

International Search Report issued in PCT/EP2012/063755 mailed on Sep. 14, 2012 (2 pages).

* cited by examiner

PROCESS FOR REMOVING OXYGENATED CONTAMINATES FROM AN ETHYLENE STREAM

CROSS-REFERENCE TO RELATED APPLICATIONS

This application claims the benefit of PCT/EP2012/063755, filed on Jul. 13, 2012, which claims priority from EP 11290349.7, filed on Jul. 28, 2011.

FIELD OF THE INVENTION

The present invention is a process for removing oxygenated contaminants from an ethylene stream.

Olefins are traditionally produced from petroleum feedstocks by catalytic or steam cracking processes. These cracking processes, especially steam cracking, produce light olefin(s), such as ethylene and/or propylene, from a variety of hydrocarbon feedstock. Ethylene and propylene are important commodity petrochemicals useful in a variety of processes for making plastics and other chemical compounds. The limited supply and increasing cost of crude oil has prompted the search for alternative processes for producing hydrocarbon products.

Olefins can be produced by dehydration of the corresponding alcohol. Ethanol can be obtained by fermentation of carbohydrates. Made up of organic matter from living organisms, biomass is the world's leading renewable energy source. The effluent produced by the ethanol dehydration comprises essentially unconverted ethanol, water, ethylene, acetaldehyde. Acetaldehyde may cause problems in ethylene recovery operations. It may comprise also very small amounts of ethane, CO, CO2, H2, CH4 and C3+ hydrocarbons. The weight ratio of ethane+CO+CO2+H2+CH4+C3+ hydrocarbons to ethylene is most of time less than 20/80.

BACKGROUND OF THE INVENTION

US 20030098281 A1 describes a method of controlling water and/or oxygenate concentrations of an olefin stream. The method includes contacting the olefin stream with a liquid absorbent. The liquid absorbent is selected from the group consisting of a polyol, amine, amide, nitrile, heterocyclic nitrogen containing compound, and mixtures thereof. A gaseous stream comprising essentially steam, ethylene, propylene and less than 2 w % of oxygenates is condensed in a quench tower. The overhead of said quench tower is washed with a caustic solution to remove CO2 and then contacted with the liquid absorbent to remove the oxygenates.

WO 03 020670 A1 provides a method for removing oxygenated components such as acetaldehyde, CO2 and/or water from an olefin stream. It explains it is desirable to remove such oxygenated components, since they may poison catalysts that are used to further process olefin composition. In addition, the presence of certain oxygenated compounds, such as acetaldehyde, can cause fouling in other olefin purification units, e.g., acid gas treating units. The method comprises providing an olefin stream containing ethylene, propylene, C4+ olefins and acetaldehyde. The olefin stream is separated into a first fraction and a second fraction, wherein the first fraction comprises at least a majority of the ethylene and/or propylene present in the olefin stream, and the second fraction comprises at least a majority of the C4+ olefins and acetaldehyde present in the olefin stream. The first fraction is then acid gas treated by sodium hydroxide or potassium hydroxide. The olefin stream is separated by distillation, preferably, the distillation is extractive distillation using an extractant. The preferred extractant is a polar composition having an average boiling point of at least 38° C. at 1 atm. Methanol is one type of preferred extractant.

WO 03 020672 A1 describes method of removing dimethyl ether from an ethylene and/or propylene containing stream. The olefin stream is passed to a water absorption column, methanol is used as the water absorbent. Methanol and entrained water, as well as some oxygenated hydrocarbon, is recovered as the bottoms stream of said water absorption column, an overhead olefin is recovered and sent to a distillation column. The distillation column separates ethylene and propylene, as well as lighter boiling point components from the dimethyl ether and heavier boiling point components, including C4+ components and methanol remaining from the methanol wash. Additional methanol is added to the distillation column to reduce clathrate and/or free water formation in the distillation column. The ethylene and propylene containing stream exits the distillation column as overhead and the heavier boiling point components which include the dimethyl ether and C4+ components exit the distillation column as the bottoms. Ethylene and propylene then flow to a caustic wash column.

WO 03 033438 A1 describes a method for processing an olefin stream containing oxygenates and water, comprising: providing an olefin stream containing oxygenates and water; dewatering the olefin stream; compressing the dewatered olefin stream; washing the olefin stream with methanol to remove at least a portion of the oxygenate from the olefin stream; contacting the methanol washed olefin stream with water; and fractionating the water contacted olefin stream. The recovered olefin stream (washed with methanol and then with water) is further sent to an alkali wash and a drying step. The olefin stream containing oxygenates and water is the effluent of an MTO process.

U.S. Pat. No. 6,444,869 describes a process for the production of ethylene from an oxygenate conversion effluent stream. The oxygenate conversion effluent stream comprises hydrogen, methane, ethylene, ethane, propylene, propane and C4+ olefins. This effluent is compressed, treated to remove oxygenates, passed to a carbon dioxide removal zone wherein carbon dioxide is absorbed by contacting a caustic solution or by contacting an amine solution in combination with a caustic solution in a conventional manner to remove the carbon dioxide, dried, then fractionation is made through a deethanizer and a demethanizer.

US 2005-0283038 A1 described a process for producing an olefins stream from a first vapor effluent stream from an oxygenate to olefin conversion reaction, said first vapor effluent stream comprising C2 and C3 olefins, C4 hydrocarbons, and C2 to C6 carbonyl compounds. In the process, the temperature and pressure of the first vapor effluent stream are adjusted to produce a second vapor effluent stream having a pressure ranging from about 100 psig to about 350 psig (790 to 2514 kPa) and a temperature ranging from about 70° F. to about 120° F. (21 to 49° C.), said second vapor effluent stream containing about 50 wt. % or more C4 hydrocarbons based upon the total weight of C4 hydrocarbons in the first vapor effluent stream. The second vapor effluent stream is then washed with a liquid alcohol-containing stream to produce a third vapor effluent stream, whereafter the third vapor effluent stream is washed with liquid water to provide a fourth vapor effluent stream comprising the C2 and C3 olefins and about 1.0 wt. % or less C2 to C6 carbonyl compounds. In one embodiment of such a recovery process, at least part of the fourth vapor effluent stream is contacted with a basic component, such as caustic or an amine, to remove the bulk of the carbon dioxide therefrom (thus removing "acid gas" from the fourth vapor effluent stream), whereafter the $CO_2$-depleted stream is dried.

The main drawback of the above prior arts is the fouling of the caustic scrubber. The inlet gas to the caustic scrubber contains reactive oxygenates like aldehydes and ketones. These aldehydes react in the aldol condensation reaction in the caustic tower environment to form significant red oil polymers. This causes significant fouling concerns in the caustic tower which impact the unit run length. The spent caustic treatment with significant red oil polymer content is also an important concern as well as the spent caustic treatment and disposal issues. In addition there are the handling and disposal issues of red oil polymers.

It has now been discovered a process for removing oxygenated contaminants from an ethylene stream wherein there is no caustic wash to remove the CO2 and no wash column to remove the oxygenates. Oxygenates are organic compounds consisting of carbon, oxygen and hydrogen.

BRIEF SUMMARY OF THE INVENTION

The present invention is a process for removing oxygenated contaminants from an ethylene stream comprising:
a) providing a dried ethylene stream (A) comprising essentially ethylene, up to 1 w % oxygenates, ethane, CO, CO2, H2, CH4 and C3+ hydrocarbons,
b) sending said stream (A) to a C2 splitter/deethanizer to produce
a bottom stream comprising essentially ethane, oxygenates and C3+ hydrocarbons,
an overhead comprising the remaining components,
c) sending said overhead to a fixed bed CO2 adsorption zone to recover a stream essentially free of CO2,
d) sending said stream essentially free of CO2 to a demethanizer/CO stripper to recover an overhead comprising H2, CH4 and CO,
liquid ethylene at the bottoms.

In another embodiment the CO2 removal step can be made on the recovered ethylene. In said embodiment the present invention is a process for removing oxygenated contaminants from an ethylene stream comprising:
a1) providing a dried ethylene stream (A) comprising essentially ethylene, up to 1 w % oxygenates, ethane, CO, CO2, H2, CH4 and C3+ hydrocarbons,
b1) sending said stream (A) to a C2 splitter/deethanizer to produce
a bottom stream comprising essentially ethane, oxygenates and C3+ hydrocarbons,
an overhead comprising the remaining components,
c1) sending said overhead stream to a demethanizer/CO stripper to recover an overhead comprising H2, CH4 and CO,
liquid ethylene comprising CO2 at the bottoms.
d1) sending said ethylene comprising CO2 to a fixed bed CO2 adsorption zone to recover an ethylene stream essentially free of CO2.

In an embodiment the weight ratio of ethane+CO+CO2+H2+CH4+C3+ hydrocarbons to ethylene in (A) is less than 10/90.

In an embodiment the weight ratio of ethane+CO+CO2+H2+CH4+C3+ hydrocarbons to ethylene in (A) is less than 10/90 and above 0.1/99.9.

In an embodiment the weight ratio of ethane+CO+CO2+H2+CH4+C3+ hydrocarbons to ethylene in (A) is less than 5/95.

In an embodiment the proportion of oxygenates in (A) is from 50 wppm to 7000 wppm.

In an embodiment the proportion of oxygenates in (A) is up to 3000 wppm.

In an embodiment the proportion of oxygenates in (A) is up to 2000 wppm.

In an embodiment the proportion of H2 in (A) is from 5 to 1000 wppm.

In an embodiment the proportion of H2 in (A) is up to 800 wppm.

In an embodiment the proportion of H2 in (A) is up to 500 wppm.

Advantageously "dried ethylene stream" at step a) means a water content less than 5 wppm, advantageously less than 3 wppm and preferably less than 1 wppm.

In an embodiment when the dried ethylene stream (A) has been made by ethanol dehydration said stream (A) contains substantially no acetylene.

Ethylene treated in accordance with this invention is particularly suitable for use as feedstock for making alpha-olefins, ethylbenzene/styrene, ethyleneoxide/ethyleneglycol, ethylenedichloride and corresponding polymers, like polyethylene homo or copolymer (PE, EPR, EPDM etc), polystyrene (PS), styrene copolymers with butadiene, isoprene, acrylonitrile or combinations (SBS, SIS, SBR, ABS, SAN), polyesters (PET) and polyvinylchlorides (PVC)

DETAILED DESCRIPTION OF THE INVENTION

Figure 1:
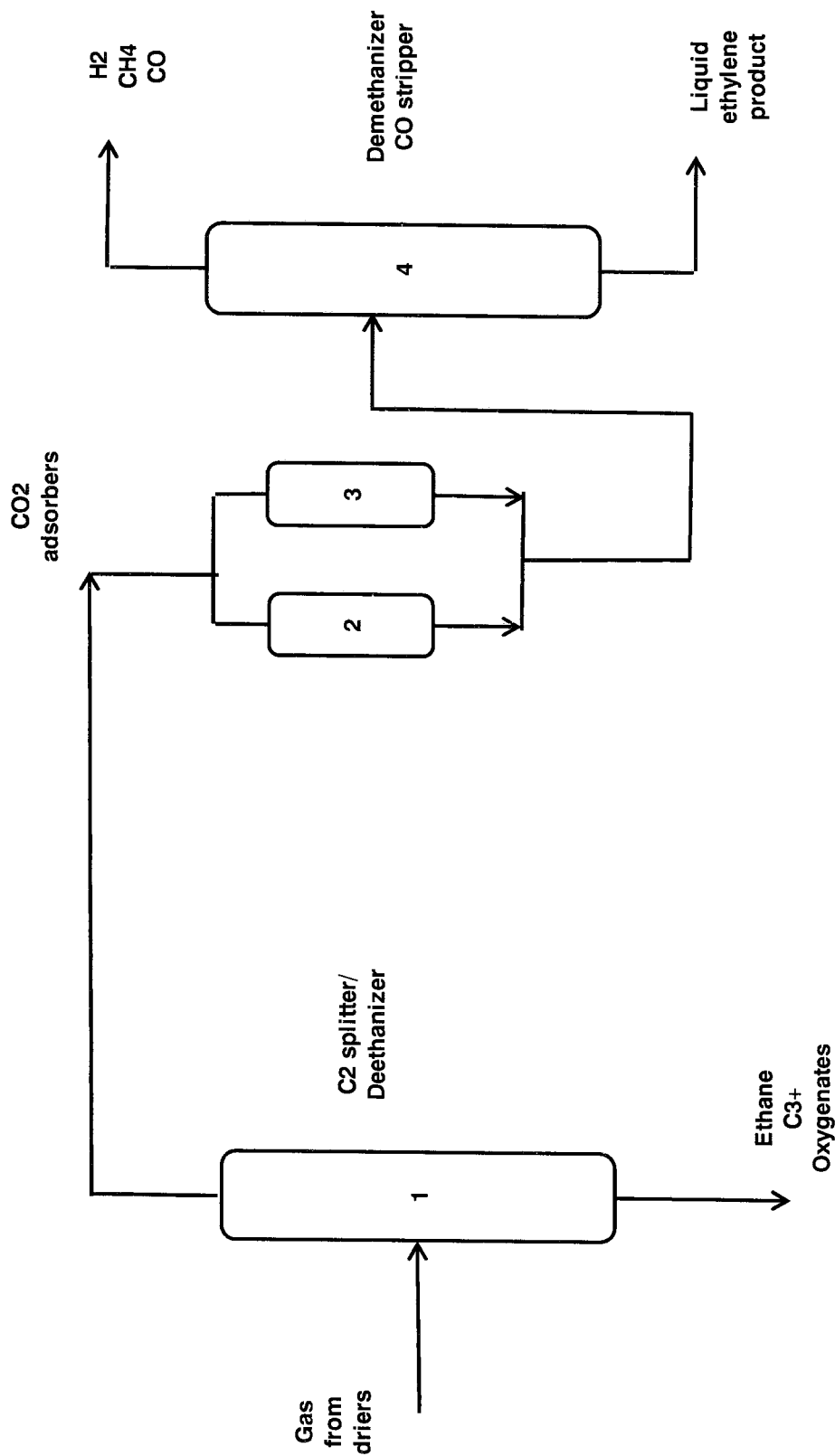
FIG. 1 depicts an embodiment with the $C_2$ splitter deethanizer, the $CO_2$ adsorbers, and the demethanizer/CO stripper.

As regards the oxygenated contaminants, also referred to as oxygenates, one can cite ethanol, C3 alcohols; ethers such as diethylether and methyl ethyl ether; carboxylic acids such as acetic acid; aldehydes such as acetaldehyde; ketones such as acetone; and esters such as methyl esters. Particularly problematic oxygenate contaminants in an alcohol dehydration are aldehydes.

As regards the ethylene stream (A) of step a), it can be originating from the dehydration of ethanol. Said dehydration can be made in one or more ethanol dehydration reactors. As regards alcohol dehydration, such process is described in WO-2009-098262, WO-2009-098267, WO-2009-098268 and WO-2009-098269 the content of which is incorporated in the present application. The present invention is very efficient for the purification of ethylene produced by dehydration of ethanol.

The outlet of said dehydration reactor comprises essentially ethylene and steam as well as minor amounts of oxygenates, ethane, CO, CO2, H2, CH4 and C3+ hydrocarbons. "Minor amounts" means the weight ratio of ethane+CO+CO2+H2+CH4+C3+ hydrocarbons to ethylene is less than 20/80 and most of time less than 10/90.

Said outlet of dehydration reactor is initially cooled, typically in a quench tower employing water as the quench medium. In the quench tower, most of the water contained in the outlet of dehydration reactor is condensed and is removed from the bottom of the tower as a liquid water bottom stream. A part of said water bottom stream is cooled in a heat exchanger and recycled as quenching medium to the top of the quench column. The part of the water bottom stream which is not recycled as quenching medium may contain a part of the oxygenates and mostly unconverted ethanol if any. Said stream can be treated in a stripping column to recover a pure water stream. Ethylene, oxygenates, ethane, CO, CO2, H2, CH4 and C3+ hydrocarbons are removed from the top of the quench tower at a pressure typically such as 1 to 16 bars absolute and are referred to as the contaminated ethylene stream. Advantageously said contaminated ethylene stream is successively compressed and cooled in one or more steps to remove the major part of water, further fed to a fixed bed drying zone and finally to the C2 splitter/deethanizer of step b).

In the previous compression steps the recovered water contains a part of the oxygenated contaminants and hydrocarbons dissolved. The contaminated hydrocarbon stream can also be cooled before the first compression step and water recovered. In an embodiment the water recovered upon each cooling further to a compression step and upon cooling, if any, before the first compression step is sent to a stripping column to produce an overhead stream comprising essentially oxygenated contaminants and hydrocarbons and an essentially pure water bottoms stream. Optionally the overhead stream is burned to destroy the oxygenated contaminants and recover heat.

After the compression steps the contaminated ethylene stream is further fed to a fixed bed drying zone and finally to the C2 splitter/deethanizer of step b). The fixed bed drying zone is known in itself.

As regards the C2 splitter/deethanizer of step b), it is advantageously a distillation column. The overhead is a mixture of ethylene, CO, CO2, H2 and CH4.

As regards the fixed bed CO2 adsorption zone of step c), it can be any component capable to selectively remove CO2. By way of example it is an available commercial fixed bed adsorption (PSA for pressure swing adsorption or TSA for temperature swing adsorption) using molecular sieves or basic oxides, supported basic oxides, high surface area carbons, organo-metallic framework components (MOF's) or mixture thereof. The molecular sieves are preferably low silica zeolites, having 8 (among which zeolite A) or 12 membered (among which zeolite X) rings and exchanged with alkali, alkaline earth or lanthanide cations. Other molecular sieves are crystalline titanosilicates (ETS family materials). Supported basic oxides are preferably, alkali, alkaline earth or lanthanide oxides supported on high surface area carbons, alumina, silica, zirconia or titania. The removal of CO2 can be carried out with a liquid stream or with a gaseous ethylene stream depending on the pressure and temperature. A stream essentially free of CO2 is recovered. As only trace amounts of CO2 have to be removed from the ethylene, the preferred process cycle is of the thermal swing adsorption (TSA) type. Said fixed bed adsorbent, once saturated with CO2, can be regenerated, during regeneration the desorption produces a stream which can be treated anywhere. In a TSA process cycle, the regeneration is done while sweeping the saturated adsorbent with an inert gas by increasing the temperature until desorption of the CO2 occurs. Eventually the saturated adsorbent can be replaced by new adsorbent and the saturated adsorbent either be disposed of or regenerated ex-situ for further use. "Essentially" has to be interpretated in the light of the further use of ethylene. Should ethylene to be polymerized CO2 has to be 1 ppm vol or less and preferably 0.5 ppm vol or less.

As regards the demethanizer, purpose is to recover an overhead comprising H2, CH4 and CO and liquid ethylene at the bottoms. It is advantageously a distillation column.

As regards the operating conditions, The demethanizer of step d) has to be at a pressure high enough to operate at temperatures which are not too low. A demethanizer to recover an overhead comprising H2, CH4 and CO and liquid ethylene at the bottoms operating at 40 barg has an overhead temperature of around 0 to −10° C. and a bottom temperature of around 0° C. The same demethanizer operating at 21 barg has an overhead temperature of −30° C. and a bottom temperature of around −24° C.

These temperatures and pressures are a function of the proportion of H2, CH4 and CO in the ethylene stream (A) and mainly of the proportion of H2. The proportion of H2, CH4 and CO in the ethylene stream (A) and mainly the proportion of H2 governs also the pressure and temperature of the C2 splitter/deethanizer located upstream said demethanizer.

In an embodiment the pressure of step b) is selected to have a temperature of the C2 splitter/deethanizer bottoms such as there is no oligomerization or polymerization of the oxygenates. By way of example said temperature should not exceed 150° C. and advantageously not exceed 100° C. This temperature is function of the pressure and of the proportion of oxygenates in the mixture of oxygenates+ethane+C3+ hydrocarbons. The higher the proportion of oxygenates the higher the temperature. The higher the pressure the higher the temperature.

In an embodiment the C2 splitter/deethanizer and the demethanizer are operating at the same pressure except the pressure drop between the C2 splitter/deethanizer and the demethanizer for transfer of fluids. Advantageously the pressure is ranging from 15 to 45 barg. In this embodiment the contaminated ethylene stream coming from the quench column is advantageously compressed in two to four compression stages in series (depending on dehydration reactor pressure), sent to the driers and finally to the C2 splitter deethanizer.

Said embodiment is described on FIG. 1 wherein (1) is the C2 splitter deethanizer, (2) and (3) the CO2 adsorbers and (4) the demethanizer/CO stripper. The contaminated ethylene stream from the quench column has been dried and sent to the C2 splitter deethanizer (1) to produce a bottom stream comprising essentially ethane, oxygenates and C3+ hydrocarbons and an overhead comprising ethylene, CO, CO2, H2 and CH4 (condenser, decanter and reflux of C2 splitter deethanizer are not shown, reboiler of C2 splitter deethanizer is not shown). Said overhead is sent to the CO2 adsorbers (2) and (3) to recover a stream essentially free of CO2 and then to the demethanizer/CO stripper (4) to recover an overhead comprising H2, CH4 and CO and liquid ethylene at the bottoms. Condenser, decanter and reflux of the demethanizer/CO stripper are not shown, reboiler of the demethanizer/CO stripper is not shown.

In a specific example according to FIG. 1 the pressure of the C2 splitter/deethanizer is around 15 to 25 barg, the top of said splitter/deethanizer is at a temperature around −20° C. to −30° C., condensed at a temperature in the range −20° C. to −30° C., the temperature on bottoms of said splitter/deethanizer is around 70 to 90° C., the pressure of the demethanizer/CO stripper around 15 to 25 barg, the top of the demethanizer/CO stripper is around −15° C. to −35° C., is condensed at a temperature around −15 to −35° C. and the temperature on bottoms of the demethanizer/CO stripper is around −15° C. to −35° C.

Advantageously the pressure of the C2 splitter/deethanizer is around 18 to 25 barg, the top of said splitter/deethanizer is at a temperature around −18° C. to −28° C., condensed at a temperature in the range −18° C. to −28° C., the temperature on bottoms of said splitter/deethanizer is around 75 to 85° C., the pressure of the demethanizer/CO stripper around 18 to 25 barg, the top of the demethanizer/CO stripper is around −20° C. to −30° C., is condensed at a temperature around −20 to −30° C. and the temperature on bottoms of the demethanizer/CO stripper is around −20° C. to −30° C.

In an embodiment the pressure of the C2 splitter/deethanizer is lower than the pressure of the demethanizer/CO stripper. Advantageously the pressure of the C2 splitter/deethanizer is ranging from 15 to 25 barg and simultaneously the pressure difference between the demethanizer/CO stripper and the C2 splitter/deethanizer is ranging from 10 to 25 barg In this embodiment the contaminated ethylene stream coming from the quench column is advantageously compressed in two to three compression stages in series, sent to the driers and finally to the C2 splitter deethanizer. Then the overhead of the C2 splitter deethanizer is compressed and sent through the CO2 adsorbers to the demethanizer/CO stripper. Optionally the essentially CO2 free stream leaving the fixed bed CO2 adsorption zone is cooled, sent to a decanter to produce a liquid phase sent as a reflux to the C2 splitter/deethanizer and a gaseous phase sent to the demethanizer/CO stripper.

Figure 2:
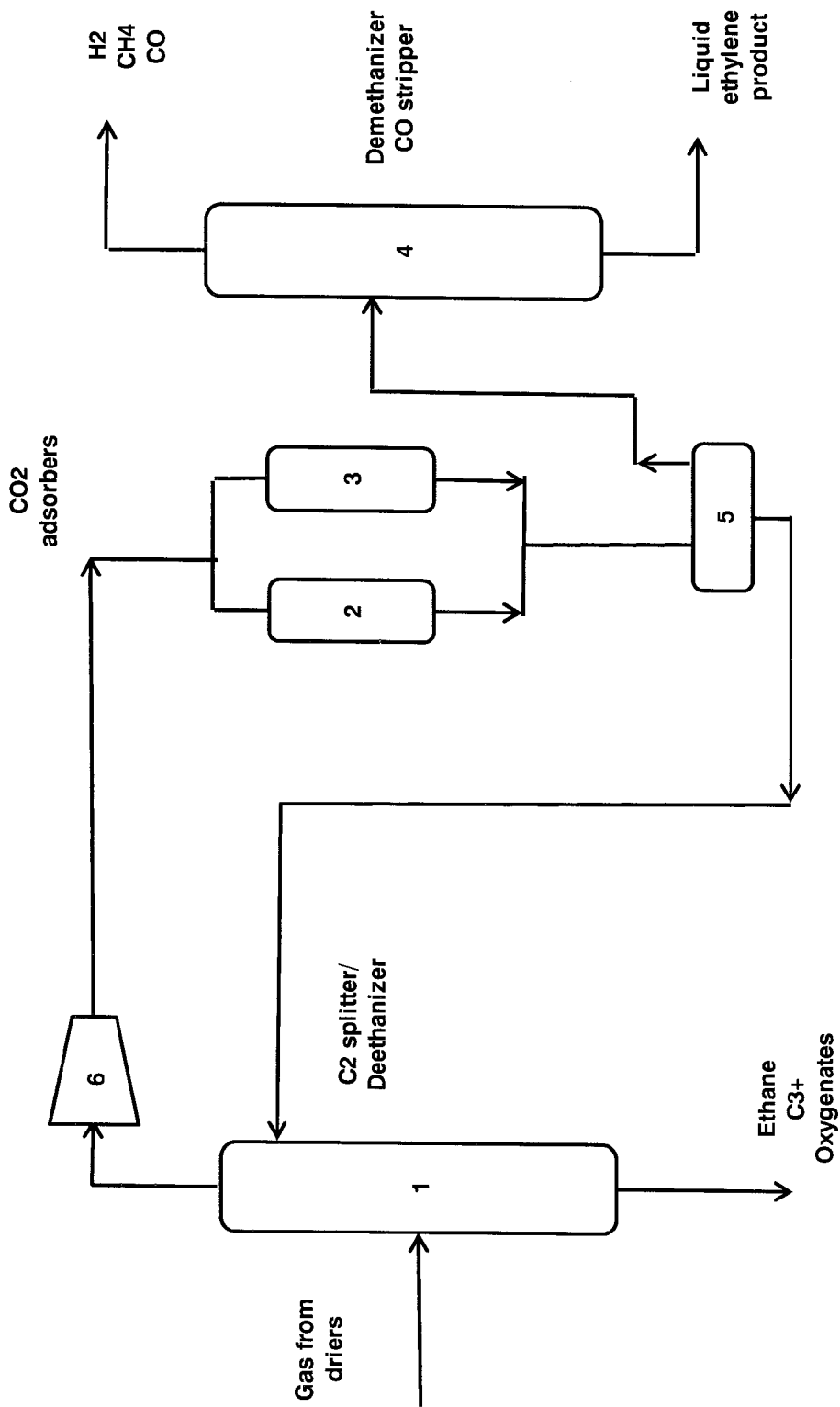
FIG. 2 depicts an embodiment in which the pressure of the $C_2$ splitter/deethanizer is lower than the pressure of the demethanizer/CO stripper.

Said embodiment is described on FIG. 2. The contaminated ethylene stream from the quench column has been dried and sent at a pressure around 15 to 25 barg to the C2 splitter deethanizer (1) to produce a bottom stream (the reboiler is not shown) comprising essentially ethane, oxygenates and C3+ hydrocarbons and an overhead comprising ethylene, CO, CO2, H2 and CH4. Said overhead (top of the the C2 splitter deethanizer) is sent to the compressor (6) to increase the pressure with 10 to 25 barg over the C2 splitter/deethanizer pressure, optionally cooled (the cooler is not shown) and sent to the CO2 adsorbers (2) and (3) to recover a stream essentially free of CO2. Then said CO2 free stream is cooled (the cooler is not shown) and sent to the decanter (5) to produce a liquid phase sent as a reflux to the C2 splitter/deethanizer (1) and a gaseous phase sent to the demethanizer/CO stripper (4). Said demethanizer/CO stripper (4) produces an overhead (the condenser, decanter and reflux are not shown) comprising H2, CH4 and CO and liquid ethylene at the bottoms (the reboiler is not shown).

Alternatively, the condenser and decanter (5) can be installed between the top outlet of the C2 splitter/deethaniser (1) and the compressor (6). The produced liquid phase is sent as a reflux to the C2 splitter/deethaniser (1) while the gaseous phase is sent to the compressor (6). In other words the contaminated ethylene stream from the quench column has been dried and sent to the C2 splitter deethanizer (1) to produce a bottom stream comprising essentially ethane, oxygenates and C3+ hydrocarbons and an overhead comprising ethylene, CO, CO2, H2 and CH4 Said overhead, the top outlet of the C2 splitter/deethaniser (1), is condensed, sent to a decanter to get a liquid phase sent as a reflux to the C2 splitter/deethaniser (1) and a gaseous phase sent to the compressor (6). Then the compressed stream is sent to the CO2 adsorbers (2) and (3) to recover a stream essentially free of CO2 and then to the demethanizer/CO stripper (4) to recover an overhead comprising H2, CH4 and CO and liquid ethylene at the bottoms.

In a specific example according to FIG. 2 the pressure of the splitter/deethanizer is around 15 to 25 barg, the temperature on top of said splitter/deethanizer around −25° C. to −35° C., the temperature on bottoms of said splitter/deethanizer around 70 to 90° C., the pressure of the demethanizer/CO stripper around 35 to 45 barg, the top of the demethanizer/CO stripper is around −10° C. to 10° C., is condensed at a temperature around −35 to −45° C. and the temperature on bottoms of the demethanizer/CO stripper is around −10 to 10° C.

Advantageously the pressure of the splitter/deethanizer is around 18 to 20 barg, the temperature on top of said splitter/deethanizer around −28° C. to −32° C., the temperature on bottoms of said splitter/deethanizer around 78 to 82° C., the pressure of the demethanizer/CO stripper around 38 to 42 barg, the top of the demethanizer/CO stripper is around −5° C. to 5° C., is condensed at a temperature around −38 to −42° C. and the temperature on bottoms of the demethanizer/CO stripper is around −2 to 2° C.

As regards the other embodiment wherein the CO2 removal step is made on the recovered ethylene, it works in a similar way as explained above in which the CO2 removal step is before the demethanizer/CO stripper.

In an embodiment the C2 splitter/deethanizer and the demethanizer are operating at the same pressure except the pressure drop between the C2 splitter/deethanizer and the demethanizer for transfer of fluids. Advantageously the pressure is ranging from 15 to 45 barg. In this embodiment the contaminated ethylene stream coming from the quench column is advantageously compressed in two to four compression stages in series (depending on dehydration reactor pressure), sent to the driers and finally to the C2 splitter deethanizer.

Figure 3:
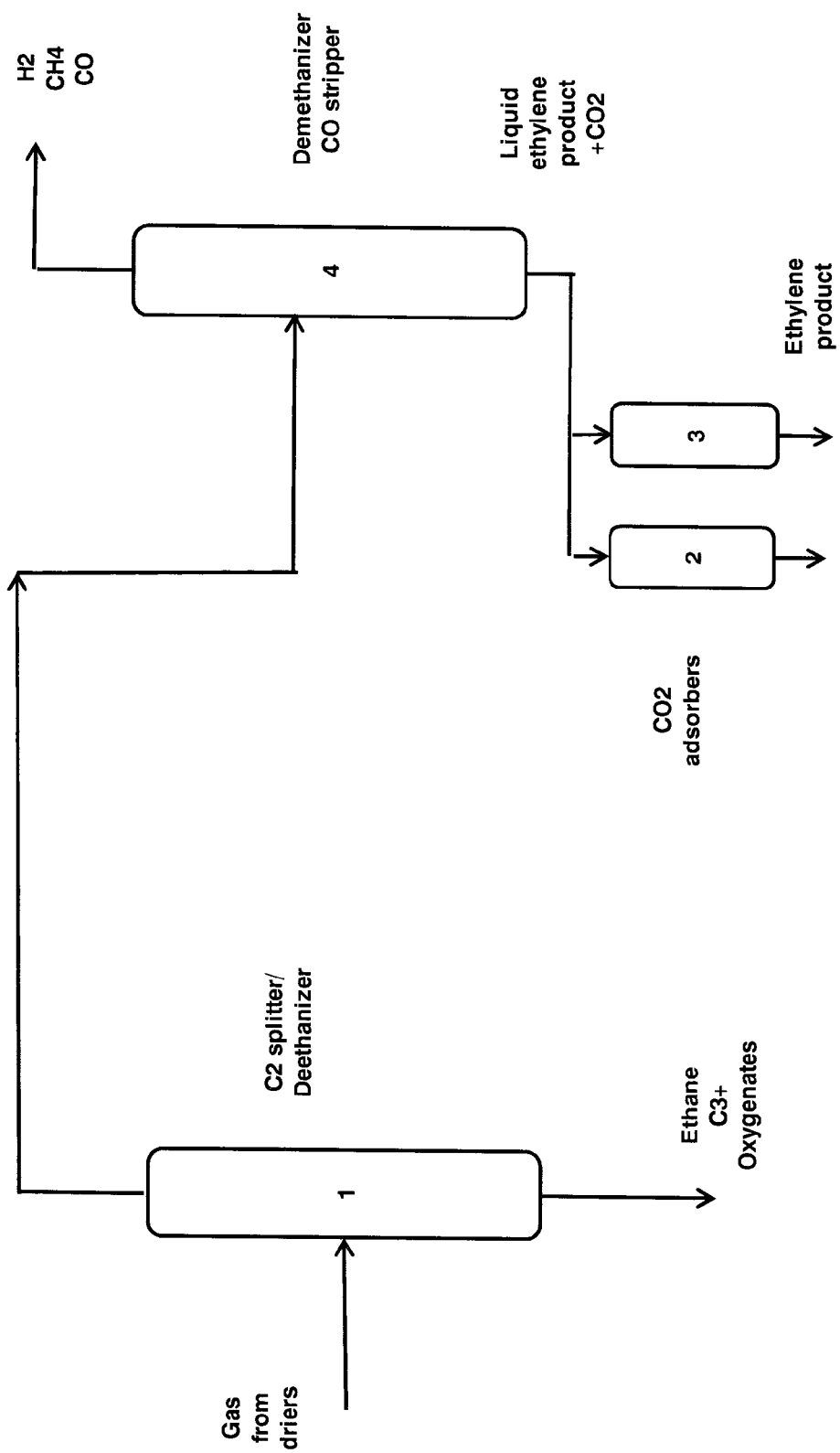
FIG. 3 depicts another embodiment with the $C_2$ splitter deethanizer, the $CO_2$ adsorbers, and the demethanizer/CO stripper.

Said embodiment is described on FIG. 3 wherein (1) is the C2 splitter deethanizer, (2) and (3) the CO2 adsorbers and (4) the demethanizer/CO stripper. The contaminated ethylene stream from the quench column has been dried and sent to the C2 splitter deethanizer (1) to produce a bottom stream (the reboiler is not shown) comprising essentially ethane, oxygenates and C3+ hydrocarbons and an overhead (the condenser, the decanter and the reflux are not shown) comprising ethylene, CO, CO2, H2 and CH4. Said overhead is sent the demethanizer/CO stripper (4) to recover an overhead (the condenser, the decanter and the reflux are not shown) comprising H2, CH4 and CO and liquid ethylene comprising CO2 at the bottoms (the reboiler is not shown). Said ethylene comprising CO2 is sent to a fixed bed CO2 adsorption zone, the CO2 adsorbers (2) and (3) to recover an ethylene stream essentially free of CO2.

In a specific example according to FIG. 3 the pressure of the C2 splitter/deethanizer is around 15 to 25 barg, the top of said splitter/deethanizer is at a temperature around −20° C. to −30° C., condensed at a temperature in the range −20° C. to −30° C., the temperature on bottoms of said splitter/deethanizer is around 70 to 90° C., the pressure of the demethanizer/CO stripper around 15 to 25 barg, the top of the demethanizer/CO stripper is around −15° C. to −35° C., is condensed at a temperature around −15 to −35° C. and the temperature on bottoms of the demethanizer/CO stripper is around −15° C. to −35° C.

Advantageously the pressure of the C2 splitter/deethanizer is around 18 to 25 barg, the top of said splitter/deethanizer is at a temperature around −18° C. to −28° C., condensed at a temperature in the range −18° C. to −28° C., the temperature on bottoms of said splitter/deethanizer is around 75 to 85° C., the pressure of the demethanizer/CO stripper around 18 to 25 barg, the top of the demethanizer/CO stripper is around −20° C. to −30° C., is condensed at a temperature around −20 to −30° C. and the temperature on bottoms of the demethanizer/CO stripper is around −20° C. to −30° C.

In an embodiment the pressure of the C2 splitter/deethanizer is lower than the pressure of the demethanizer/CO stripper. Advantageously the pressure of the C2 splitter/deethanizer is ranging from 15 to 25 barg and simultaneously the pressure difference between the demethanizer/CO stripper and the C2 splitter/deethanizer is ranging from 10 to 25 barg. In this embodiment the contaminated ethylene stream coming from the quench column is advantageously compressed in two to three compression stages in series, sent to the driers and finally to the C2 splitter deethanizer. Then the overhead of the C2 splitter deethanizer is compressed and sent to the demethanizer/CO stripper.

Figure 4:
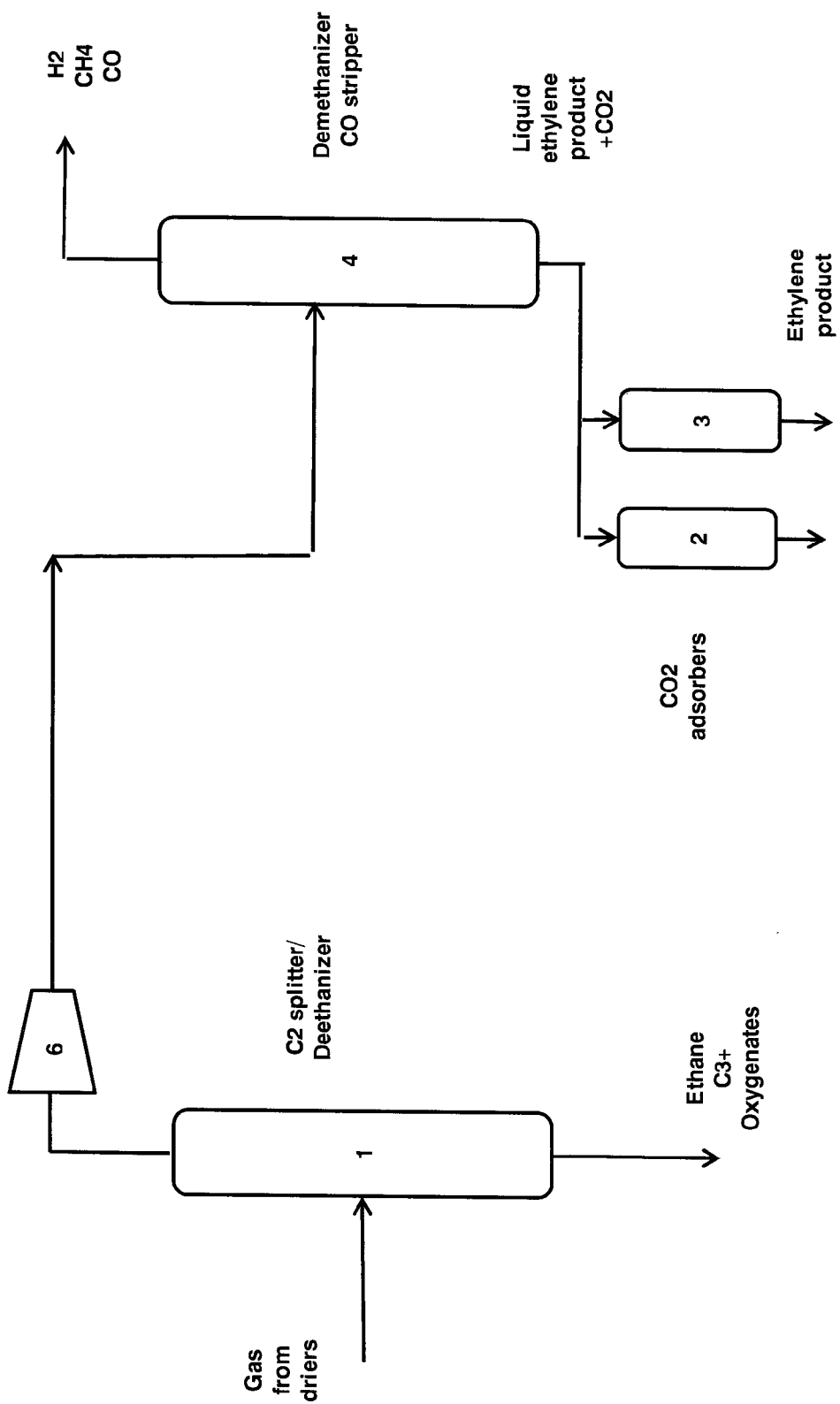
FIG. 4 depicts an embodiment with a compressor.

Said embodiment is described on FIG. 4. In addition to FIG. 3 there are additional equipment: a compressor (6). The contaminated ethylene stream from the quench column has been dried and sent at a pressure around 15 to 25 barg to the C2 splitter deethanizer (1) to produce a bottom stream (the reboiler is not shown) comprising essentially ethane, oxygenates and C3+ hydrocarbons and an overhead comprising ethylene, CO, CO2, H2 and CH4. Said overhead is condensed, sent to a decanter to get a liquid phase sent as a reflux to (1) and a gaseous phase sent to the compressor (6). Said condenser, decanter and reflux are not shown). The compressor (6) increases the pressure with 10 to 25 barg over the C2 splitter/deethanizer pressure, and the compressed stream is sent to the demethanizer/CO stripper (4). Said demethanizer/CO stripper (4) produces an overhead (the condenser, the decanter and the reflux are not shown) comprising H2, CH4 and CO and at the bottom liquid ethylene comprising CO2 (the reboiler is not shown). Said ethylene comprising CO2 is sent to a fixed bed CO2 adsorption zone, the CO2 adsorbers (2) and (3) to recover an ethylene stream essentially free of CO2.

In a specific example according to FIG. 4 the pressure of the splitter/deethanizer is around 15 to 25 barg, the top of said splitter/deethanizer is at a temperature around −25° C. to −35° C., condensed at a temperature in the range −25° C. to −35° C., the temperature on bottoms of said splitter/deethanizer is around 70 to 90° C., the pressure of the demethanizer/CO stripper around 35 to 45 barg, the top of the demethanizer/CO stripper is around −10° C. to 10° C., is condensed at a temperature around −35 to −45° C. and the temperature on bottoms of the demethanizer/CO stripper is around −10 to 10° C.

Advantageously the pressure of the splitter/deethanizer is around 18 to 20 barg, the top of said splitter/deethanizer is at a temperature around −28° C. to −32° C., the temperature on bottoms of said splitter/deethanizer around 78 to 82° C., the pressure of the demethanizer/CO stripper around 38 to 42 barg, the top of the demethanizer/CO stripper is around −5° C. to 5° C., is condensed at a temperature around −38 to −42° C. and the temperature on bottoms of the demethanizer/CO stripper is around −2 to 2° C.

EXAMPLE

Figure 5:
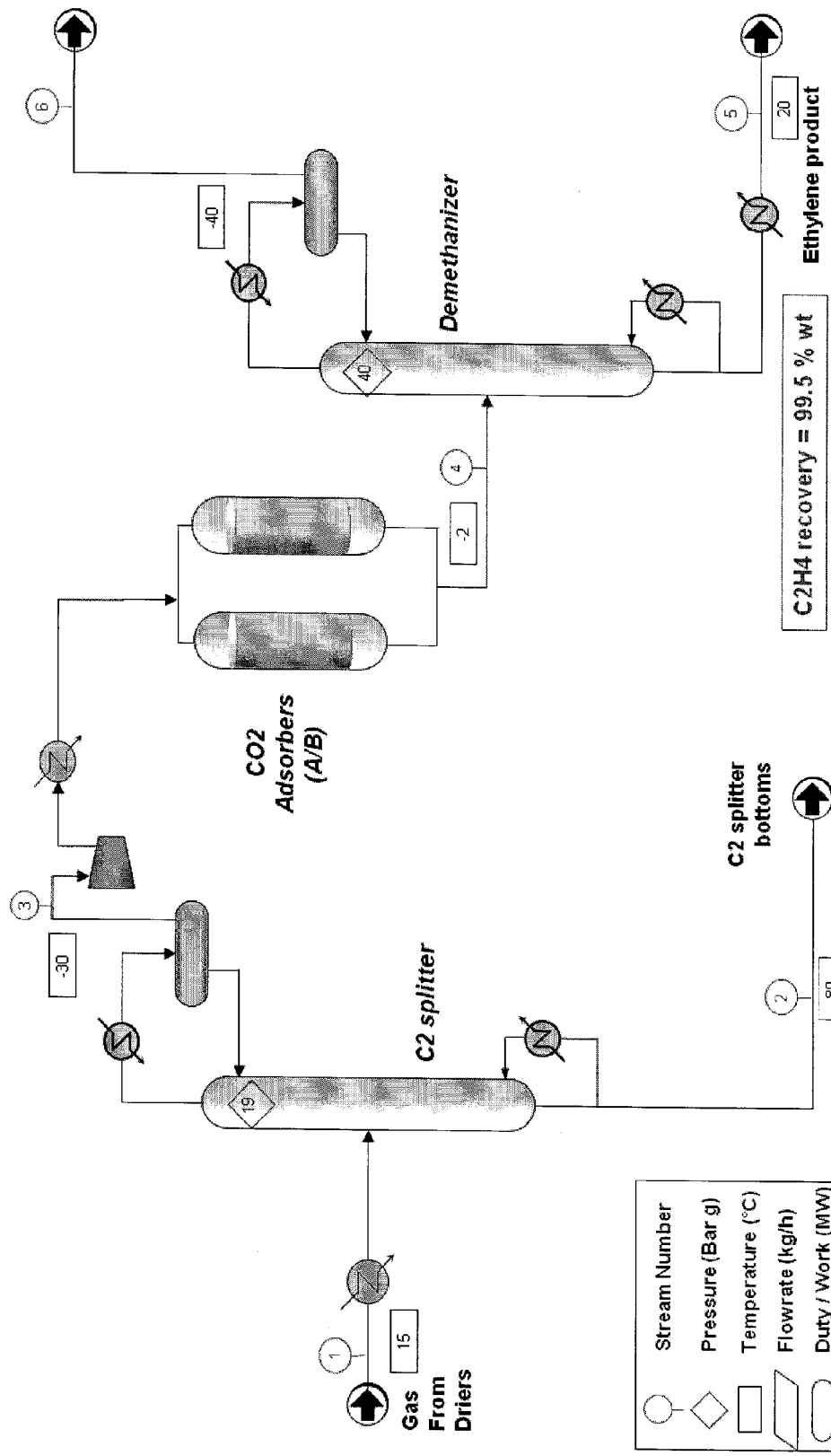
FIG. 5 depicts an embodiment derived from the embodiment shown in FIG. 2, in which the position of the condenser and decanter are changed to be located between the outlet of the $C_2$ splitter/deethaniser and the compressor.

The process according to FIG. 5 is operated. FIG. 5 is derived from FIG. 2 by changing the position of the condenser and decanter (5), they are located between the outlet of the C2 splitter/deethaniser and the compressor. The results are on the following table.

| | | stream No on FIG. 5 | | | | | |
|---|---|---|---|---|---|---|---|
| | | 1<br>C2 splitter<br>feed | 2<br>C2 splitter<br>bottoms | 3<br>C2 splitter<br>vapor distillat | 4<br>Demethanizer<br>feed | 6<br>Demethanizer<br>purge | 5<br>Ethylene<br>product |
| Temperature | ° C. | 15 | 80 | −30 | −2 | −40 | 20 |
| Pressure | bar g | 20 | 19 | 19 | 40 | 40 | 20 |
| H2 | kg/h | 8 | | 8 | 8 | 8 | |
| CO | kg/h | 1 | | 1 | 1 | 1 | |
| CO2 | kg/h | 1 | | 1 | | | |
| ethane | kg/h | 23 | 11 | 12 | 12 | | 12 |
| ethylene | kg/h | 25108 | 30 | 25078 | 25078 | 90 | 24988 |
| acetaldehydes | kg/h | 150 | 150 | | | | |
| C3+ | kg/h | 715 | 715 | | | | |
| Total | kg/h | 26006 | 906 | 25100 | 25099 | 99 | 25000 |

The invention claimed is:

1. A process for removing oxygenated contaminants from an ethylene stream comprising:
   a) providing a dried ethylene stream (A) comprising essentially ethylene, up to 1 w % oxygenates, ethane, CO, $CO_2$, $H_2$, $CH_4$ and $C_{3+}$ hydrocarbons;
   b) sending the dried ethylene stream (A) to a $C_2$ splitter/deethanizer to produce a bottom stream comprising essentially ethane, oxygenates and $C_{3+}$ hydrocarbons; and an overhead comprising the remaining components;
   c) sending the overhead from the $C_2$ splitter/deethanizer to a fixed bed $CO_2$ adsorption zone to recover a stream essentially free of $CO_2$;
   d) sending the stream from the fixed bed $CO_2$ adsorption zone, wherein the stream is essentially free of $CO_2$, directly to a demethanizer/CO stripper without passing the stream through a wash column or a caustic wash to recover an overhead comprising $H_2$, $CH_4$ and CO; and liquid ethylene at the bottoms.

2. The process of claim 1, wherein the $C_2$ splitter/deethanizer and the demethanizer operate at the same pressure, except a pressure drop between the $C_2$ splitter/deethanizer and the demethanizer for transfer of fluids, wherein the pressure ranges from 15 to 45 barg.

3. The process of claim 1, wherein a pressure of the $C_2$ splitter/deethanizer is lower than a pressure of the demethanizer/CO stripper, wherein the pressure of the $C_2$ splitter/ deethanizer ranges from 15 to 25 barg, and a pressure difference between the demethanizer/CO stripper and the $C_2$ splitter/deethanizer ranges from 10 to 25 barg.

4. The process according to claim 3, wherein the overhead of the $C_2$ splitter/deethaniser is condensed, sent to a decanter to obtain a liquid phase that is sent as a reflux to said $C_2$ splitter/deethaniser and to obtain a gaseous phase that is sent to a compressor to obtain a compressed stream that is sent to the $CO_2$ adsorption zone.

5. The process of claim 3, wherein the overhead of the $C_2$ splitter/deethaniser is sent to a compressor, optionally cooled and sent to the $CO_2$ adsorption zone to recover a stream essentially free of $CO_2$;
wherein the stream essentially free of $CO_2$ is cooled and sent to a decanter to produce a liquid phase that is sent as a reflux to the $C_2$ splitter deethanizer and to produce a gaseous phase that is sent to the demethanizer/CO stripper.

6. The process of claim 1, wherein a weight ratio of ethane+CO+$CO_2$+$H_2$+$CH_4$+$C_{3+}$ hydrocarbons to ethylene in the dried ethylene stream (A) is less than 10/90.

7. The process of claim 1, wherein a weight ratio of ethane+CO+$CO_2$+$H_2$+$CH_4$+$C_{3+}$ hydrocarbons to ethylene in the dried ethylene stream (A) is less than 10/90 and above 0.1/99.9.

8. The process of claim 1, wherein a weight ratio of ethane+CO+$CO_2$+$H_2$+$CH_4$+$C_{3+}$ hydrocarbons to ethylene in the dried ethylene stream (A) is less than 5/95.

9. The process of claim 1, wherein a proportion of oxygenates in the dried ethylene stream (A) is from 50 wppm to 7000 wppm.

10. The process of claim 1, wherein a proportion of oxygenates in the dried ethylene stream (A) is up to 3000 wppm.

11. The process of claim 1, wherein a proportion of oxygenates in the dried ethylene stream (A) is up to 2000 wppm.

12. The process of claim 1, wherein a proportion of $H_2$ in the dried ethylene stream (A) is from 5 to 1000 wppm.

13. The process of claim 1, wherein a proportion of $H_2$ in the dried ethylene stream (A) is up to 800 wppm.

14. The process of claim 1, wherein a proportion of $H_2$ in the dried ethylene stream (A) is up to 500 wppm.

15. The process of claim 1, wherein the dried ethylene stream (A) originates from the dehydration of ethanol.

16. A process for removing oxygenated contaminants from an ethylene stream comprising:
a1) providing a dried ethylene stream (A) comprising essentially ethylene, up to 1 w % oxygenates, ethane, CO, $CO_2$, $H_2$, $CH_4$ and $C_{3+}$ hydrocarbons;
b1) sending the dried ethylene stream (A) to a $C_2$ splitter/deethanizer to produce a bottom stream comprising essentially ethane, oxygenates and $C_{3+}$ hydrocarbons; and an overhead comprising the remaining components;
c1) sending the overhead stream to a demethanizer/CO stripper to recover an overhead comprising $H_2$, $CH_4$ and CO; and a liquid ethylene stream at the bottoms, wherein the liquid ethylene stream comprises $CO_2$;
d1) sending the liquid ethylene stream from the demethanizer/CO stripper directly to a fixed bed $CO_2$ adsorption zone without passing the liquid ethylene stream through a wash column or a caustic wash to recover an ethylene stream essentially free of $CO_2$.

17. The process of claim 16, wherein the $C_2$ splitter/deethanizer and the demethanizer operate at the same pressure, except a pressure drop between the $C_2$ splitter/deethanizer and the demethanizer for transfer of fluids, and wherein the pressure ranges from 15 to 45 barg.

18. The process of claim 16, wherein a pressure of the $C_2$ splitter/deethanizer is lower than a pressure of the demethanizer/CO stripper;
wherein the pressure of the $C_2$ splitter/deethanizer ranges from 15 to 25 barg; and
wherein a pressure difference between the demethanizer/CO stripper and the $C_2$ splitter/deethanizer ranges from 10 to 25 barg.

19. The process of claim 16, wherein the overhead of the $C_2$ splitter/deethaniser is condensed and sent to a decanter to obtain a liquid phase that is sent as a reflux to said $C_2$ splitter/deethaniser and to obtain a gaseous phase that is sent to a compressor to obtain a compressed stream that is sent to the demethanizer/CO stripper.

20. The process of claim 16, wherein a weight ratio of ethane+CO+$CO_2$+$H_2$+$CH_4$+$C_{3+}$ hydrocarbons to ethylene in the dried ethylene stream (A) is less than 10/90.

21. The process of claim 16, wherein a weight ratio of ethane+CO+$CO_2$+$H_2$+$CH_4$+$C_{3+}$ hydrocarbons to ethylene in the dried ethylene stream (A) is less than 10/90 and above 0.1/99.9.

22. The process of claim 16, wherein a weight ratio of ethane+CO+$CO_2$+$H_2$+$CH_4$+$C_{3+}$ hydrocarbons to ethylene in the dried ethylene stream (A) is less than 5/95.

23. The process of claim 16, wherein a proportion of oxygenates in the dried ethylene stream (A) is from 50 wppm to 7000 wppm.

24. The process of claim 16, wherein a proportion of oxygenates in the dried ethylene stream (A) is up to 3000 wppm.

25. The process of claim 16, wherein a proportion of oxygenates in the dried ethylene stream (A) is up to 2000 wppm.

26. The process of claim 16, wherein a proportion of $H_2$ in the dried ethylene stream (A) is from 5 to 1000 wppm.

27. The process of claim 16, wherein a proportion of $H_2$ in the dried ethylene stream (A) is up to 800 wppm.

28. The process of claim 16, wherein a proportion of $H_2$ in the dried ethylene stream (A) is up to 500 wppm.

29. The process of claim 16, wherein the dried ethylene stream (A) originates from the dehydration of ethanol.

* * * * *